(12) United States Patent
Merea

(10) Patent No.: US 9,389,117 B2
(45) Date of Patent: Jul. 12, 2016

(54) SUCCESSIVE TARE SCALE SYSTEM AND METHOD

(71) Applicant: The Orange Chef Company, San Francisco, CA (US)

(72) Inventor: Santiago Merea, San Francisco, CA (US)

(73) Assignee: THE ORANGE CHEF COMPANY, San Francisco, CA (US)

( * ) Notice: Subject to any disclaimer, the term of this patent is extended or adjusted under 35 U.S.C. 154(b) by 63 days.

(21) Appl. No.: 13/909,011

(22) Filed: Jun. 3, 2013

(65) Prior Publication Data

US 2014/0356492 A1    Dec. 4, 2014

(51) Int. Cl.
| | |
|---|---|
| *A23L 1/00* | (2006.01) |
| *A47J 43/00* | (2006.01) |
| *G01G 19/414* | (2006.01) |
| *G01G 19/415* | (2006.01) |
| *G06F 19/00* | (2011.01) |
| *G06Q 10/10* | (2012.01) |
| *A23L 1/48* | (2006.01) |
| *G09B 19/00* | (2006.01) |

(52) U.S. Cl.
CPC ........... *G01G 19/414* (2013.01); *A23L 1/00* (2013.01); *G01G 19/415* (2013.01); *G06Q 10/10* (2013.01); *A23L 1/48* (2013.01); *A47J 43/00* (2013.01); *G01G 19/4146* (2013.01); *G06F 19/3475* (2013.01); *G09B 19/0092* (2013.01)

(58) Field of Classification Search
CPC ............ A23L 1/48; A23L 1/00; A23L 1/01; A47J 43/00; G01G 19/00; G01G 19/414; G01G 19/4146; G01G 17/06; G01G 19/415; G09B 19/0092; G06F 19/3475; Y10S 128/921; G06Q 10/10
See application file for complete search history.

(56) References Cited

U.S. PATENT DOCUMENTS 4,840,239 A * 6/1989 Slagg ..................... 177/25.14
5,544,684 A * 8/1996 Robinette, III ......... 177/25.14
(Continued)

FOREIGN PATENT DOCUMENTS

| | | |
|---|---|---|
| JP | 200510951 | 1/2005 |
| WO | 0238456 | 5/2002 |

OTHER PUBLICATIONS

My Recipe Book,"Typing Recipes into the App", Oct. 5, 2012, Retrieved on Apr. 9, 2013 from http://www.myrecipebookapp.com/?p=90 , 2 pages.
(Continued)

*Primary Examiner* — Randy W Gibson
(74) *Attorney, Agent, or Firm* — Sheppard Mullin Richter & Hampton LLP

(57) ABSTRACT

This disclosure relates to a system configured to determine masses, weights, and/or other quantities of individual ingredients added to a food dish during preparation. At least some of the components of the system may be configured to be used in a food preparation area. The system may include a scale, a client computing device, external resources, and/or other components. The system may be configured to weigh and/or determine the mass of individual ingredients of the dish as the ingredients are added to the dish. The system may be configured to determine the individual mass and/or weight of each ingredient based on the masses and/or weights of individual ingredients previously added to the dish and/or a current mass and/or weight of the dish as a given ingredient is added.

32 Claims, 6 Drawing Sheets

(56) References Cited

U.S. PATENT DOCUMENTS

| | | | |
|---|---|---|---|
| 5,934,181 | A | 8/1999 | Adamczewski |
| 6,412,398 | B1 | 7/2002 | Norcross |
| 6,837,148 | B1* | 1/2005 | Deschenes ............... A47J 27/00 99/325 |
| 6,978,221 | B1* | 12/2005 | Rudy ............................ 702/173 |
| 6,982,640 | B2 | 1/2006 | Lindsay |
| 7,292,146 | B1 | 11/2007 | Nguyen |
| 7,409,765 | B2 | 8/2008 | So |
| 7,523,302 | B1 | 4/2009 | Brown et al. ................. 713/155 |
| 7,620,568 | B1 | 11/2009 | Parker-Malchak |
| 7,680,691 | B2 | 3/2010 | Kimball |
| 8,200,548 | B2 | 6/2012 | Wiedl ........................... 705/26.5 |
| 8,235,724 | B2 | 8/2012 | Gilley |
| 8,636,516 | B2* | 1/2014 | Batsikouras .................. 434/127 |
| 8,770,983 | B2* | 7/2014 | Batsikouras .................. 434/127 |
| 8,829,365 | B1* | 9/2014 | Wallace et al. ............... 434/127 |
| 2003/0159857 | A1 | 8/2003 | Lin |
| 2004/0118618 | A1* | 6/2004 | Davidson et al. ........... 177/25.13 |
| 2009/0009815 | A1 | 1/2009 | Karasik et al. ................ 358/403 |
| 2009/0144081 | A1* | 6/2009 | Harlan ................... G06Q 50/22 705/2 |
| 2009/0157752 | A1 | 6/2009 | Gonzalez .................... 707/104.1 |
| 2009/0258331 | A1 | 10/2009 | Do |
| 2009/0259687 | A1* | 10/2009 | Do .................... G06F 17/30867 |
| 2009/0309704 | A1 | 12/2009 | Chang |
| 2010/0038149 | A1 | 2/2010 | Corel |
| 2010/0125181 | A1* | 5/2010 | Hyde et al. .................... 600/300 |
| 2010/0240962 | A1 | 9/2010 | Contant |
| 2011/0044370 | A1 | 2/2011 | Schochet |
| 2011/0167100 | A1* | 7/2011 | Brodowski ................ A23L 1/00 708/105 |
| 2011/0168456 | A1* | 7/2011 | Sharawi et al. ............. 177/25.16 |
| 2011/0213667 | A1 | 9/2011 | Ierullo |
| 2012/0136864 | A1 | 5/2012 | Ochtel ........................... 707/738 |
| 2012/0179665 | A1 | 7/2012 | Baarman |
| 2013/0029298 | A1 | 1/2013 | Batsikouras |
| 2013/0171304 | A1 | 7/2013 | Huntley |
| 2013/0209972 | A1 | 8/2013 | Carter |
| 2013/0216982 | A1 | 8/2013 | Bennett |
| 2013/0268111 | A1 | 10/2013 | Dekar |
| 2014/0318874 | A1* | 10/2014 | Moses ................... G01G 19/414 177/1 |
| 2014/0332289 | A1* | 11/2014 | Gallagher, Jr. ............. 177/25.13 |
| 2015/0260699 | A1* | 9/2015 | Minvielle ............... G01N 33/02 426/231 |
| 2015/0305564 | A1* | 10/2015 | Jimenez ................ A47J 43/046 366/141 |
| 2015/0325142 | A1* | 11/2015 | Ghalavand ......... G09B 19/0092 434/127 |
| 2016/0037966 | A1* | 2/2016 | Chin ........................ A23L 1/01 426/231 |

OTHER PUBLICATIONS

Turnage, Will, "Kitchen Scale App Prototype", http://www.youtube.com/watch?v=S5WNCv4cqfg Apr. 22, 2012, Retrieved on Jun. 3, 2013, 3 pages.

Trew, James "HAPILABS introduces HAPIfork (and spoon) smart utensils, brings metrics to your mouthfuls (hands-on)",http://www.engadget.com/2013/01/06/hapilabs-introduces-hapifork-andspoon-smart-utensils-brings/, Jan. 6, 2013, retrieved Feb. 20, 2014.

Seth, Radhika, "Tasy Tasings", http://www.yankodesign.com/2012/10/23/tasty-tastings/, Oct. 23, 2012, retrieved Feb. 20, 2014.

Comstock, Jonah, "Lift Labs raises $1M for tremor-canceling spoon", http://mobihealthnews.com/25502/lift-labs-raises-1m-for-tremor-canceling-spoon/.

"French Digital Kitchen", http://digitalinstitute.ncl.ac.uk/ilablearnkitchen/, retrieved Feb. 20, 2014.

Hooper, Clare, Clare Hooper\s Blog, "More activity recognition" http://www.clarehooper.net/blog/2012/04/more-activity-recognition/, Apr. 17.

Pham, Coung et al., "The Ambient Kitchen: A Pervasive Sensing Environment for Situated Services" http://www.clarehooper.net/publications/2012/DIS2012demo.pdf, Jun. 11, 2012, retrieved Feb. 20, 2014.

Wax Sensor, http://europeandigitalkitchen.com/wp-content/uploads/2012/01/Lancook-Utensils- Brochure.pdf, retrieved Feb. 20, 2014.

Roberti, Mark, "RFID's Role in Food Safety", RFID Journal, http://www.rfidjournal.com/articles/view?10864, Jul. 29, 2013.vbTab.

Wikipedia, "Food Packaging", http://en.wikipedia.org/wiki/Food_packaging, retrieved May 16, 2014.

RFID digital weighing scales with printer, http://www.alibaba.com/productgs/614113341/LED_displayer_RFID_digital_weighing_scales.html, retrieved May 16.

Terso Solutions, "RFID Refrigerator", http://www.tersosolutions.com/rfid-refrigerators/, retrieved May 19, 2014.

Discover RFID, http://www.discoverrfid.org/what-is-possible/get-what-you-want/perfectly-cooked-recipes.html.

U.S. Appl. No. 61/800,252, filed Mar. 15, 2013.

Smart Diet Scale Features, http://smartdietscale.com/how-it-works/; retrieved on Apr. 6, 2015; 7 pages.

Watts, Tom, "Smart Diet Scale makes it easy to lose weight"; The Macomb Daily; Jan. 31, 2013, 2 pages; www.macombdaily.com.

Cheng, Jacqui, "Cooking with the IPad: Which Apps Offer the Best Experience?" Ars Technica. Conde Nast, Aug. 7, 2012. Web. Mar. 3, 2016 <http://arstechnica.com/apple/2012/08/cooking-with-the-ipad-which-apps-offer-the-best-experience/> 8 pgs.

* cited by examiner

SUCCESSIVE TARE SCALE SYSTEM AND METHOD

FIELD OF THE DISCLOSURE

This disclosure relates to a system configured to determine masses and/or weights of individual ingredients added to a dish during preparation.

BACKGROUND

Systems for generating electronic recipes are known. Systems for displaying electronic recipes during meal preparation are known. Such systems typically rely on direct input from users for recipe creation and/or step by step advancement through a displayed recipe during meal preparation. For example, users may type each ingredient and its corresponding quantity into a computer to create an electronic recipe. Users may indicate via a mouse, a touchscreen, a voice command, or a gesture that a previous recipe step is complete and the next recipe step is ready to begin.

SUMMARY

One aspect of the disclosure relates to a system configured to determine masses, weights, and/or other quantities of individual ingredients added to a food dish during preparation. At least some of the components of the system may be configured to be used in a food preparation area (e.g., a kitchen). The system may include a scale, a client computing device, external resources, and/or other components. The system may be configured to weigh individual ingredients of the dish as the ingredients are added to the dish. The system may be configured to determine the individual mass and/or weight of each ingredient based on the masses and/or weights of individual ingredients previously added to the dish and/or a current mass and/or weight of the dish as a given ingredient is added.

It should be noted that describing the functionality of the system using ingredients during the preparation of a food dish is not intended to be limiting. The system may be used to weigh/measure masses and/or weights of other objects for other reasons. For example, the system may be used to weigh screws, nails, and bolts purchased at a hardware store. The system may be configured to determine the individual mass and/or weight of each group of purchased items based on the masses and/or weights of the groups previously placed on the scale, and/or a current mass and/or weight of a group of items as the items are placed on the scale.

Responsive to the user finishing preparation of the dish, the system may facilitate electronic storage of the individual ingredients, the corresponding masses and/or weights of the individual ingredients in the dish, and/or other information in an electronic recipe. The system may be configured to determine nutritional information for the recipe based on the ingredients, the masses and/or weights of the ingredients, and/or other information. The electronic recipe may be stored locally on the client computing device, stored on an external database, shared via social media (e.g., Facebook, Twitter), distributed via email, shared via text message, and/or shared in other ways. In some implementations, the electronic recipe may be stored in third party applications (e.g., Evernote) and/or stored in proprietary formats. In some implementations, information related to the electronic recipe may be used for data aggregation.

In some implementations, the system may be configured such that the electronic recipe may be edited by a user before storage and/or sharing. Editing may include editing text, adding photos and/or video, adding web links, directly integrating the electronic recipe with other applications (e.g., Instagram, Pinterest, etc.), and/or other customization.

In some implementations, the system may be used during preparation of a dish according to an existing electronic recipe. The system may be configured such that a user may enter and/or select the existing electronic recipe for preparation. The existing electronic recipe may be stored locally on the client computing device, stored in an external database, accessed via the internet and/or other networks, and/or be retrieved from other sources. The system may be configured to prompt a user to cease adding individual ingredients to the dish during preparation of the existing electronic recipe. The prompts may be based on current masses and/or weights of the ingredients added to the dish during preparation, target masses and/or weights of the individual ingredients specified in the electronic recipe, and/or other information.

In some implementations, the system may be configured to customize the existing electronic recipe entered and/or selected by the user. Responsive to the user adding more and/or less of one or more ingredients than the amounts specified by the existing electronic recipe, the system may customize the existing electronic recipe to reflect the actual masses and/or weights of the individual ingredients added to the dish. The system may facilitate electronic storage and/or sharing of the customized recipe.

The scale may be configured to generate output signals conveying information related to the masses and/or weights of the individual ingredients added to the dish. The scale may be located in and/or near a food preparation area. The scale may include surfaces configured to be wiped off and/or cleaned, touch sensitive and/or physical buttons that may be utilized by a user whose finger may be dirtied by food preparation, and/or other features of a scale designed for use in a food preparation area. In some implementations, the full surface area of the scale may be touch sensitive. In some implementations, the scale may be portable. In some implementations, the scale may be controlled via the client computing device.

The client computing device may be configured such that a user may access the system via the client computing device. The client computing device may include a user interface, one or more processors, electronic storage, and/or other components. By way of non-limiting example, a given client computing device may include one or more of a desktop computer, a laptop computer, a handheld computer, a tablet computing platform, a NetBook, a smartphone, and/or other computing platforms.

The user interface may be configured to receive entry and/or selection of ingredient information indicating which individual ingredient is currently being added to the dish during preparation. In some implementations, the user interface may be configured to receive entry and/or selection of an electronic recipe for preparation by the user. The electronic recipe may specify target masses and/or weights of the individual ingredients in the dish.

The processor may be configured to execute computer program modules. The computer program modules may include an ingredient module, a mass module, a recipe module, a nutrition module, a customization module, and/or other modules.

The ingredient module may be configured to obtain ingredient information indicating which individual ingredient is currently being added to the dish. The ingredient information may be obtained from a user via the user interface, obtained via the external resources, and/or obtained via in other ways. In some implementations, the ingredient module may be configured such that obtaining the ingredient information via the external resources may include reading, scanning, and/or optically recognizing information that identifies an individual ingredient. For example, the external resources may include a scanner configured to recognize a bar code and/or other identifying information included on the packaging of an individual ingredient. The external resources may include optical recognition equipment configured to optically recognize individual ingredients.

The mass module may be configured to determine the masses and/or weights of the individual ingredients added to the dish. The determinations may be based on the output signals from the scale. The mass and/or weight determinations for the individual ingredients may be made by the mass module without intervention via the scale and/or the client computing device by the user. The mass and/or weight determinations for the individual ingredients may be made with the previously added ingredients still on the scale as a current ingredient is being added to the dish.

The recipe module may be configured to facilitate electronic storage of the individual ingredients and/or the corresponding masses and/or weights of the individual ingredients added to the dish in an electronic recipe. The electronic recipe may be stored locally on the client computing device, stored remotely via the external resources, and/or stored in other locations. In some implementations, the recipe module may be configured to facilitate sharing of the electronic recipe via social media (e.g., Facebook, Twitter), distribution of the electronic recipe via email, posting of the electronic recipe to a blog and/or other websites, sharing of the electronic recipe via text message, and/or sharing in other ways In some implementations, the recipe module may be configured to facilitate entry, selection, viewing, and/or following of previously stored electronic recipes via the user interface. The electronic recipes may specify target masses and/or weights of individual ingredients in a dish. In some implementations, the recipe module may be configured to, responsive to the masses and/or weights of the individual ingredients added to the dish reaching the target masses and/or weights of the individual ingredients specified by the recipe, control the user interface to prompt the user to cease adding the individual ingredients.

The nutrition module may be configured to determine nutritional information for the dish. The nutrition module may be configured to determine nutritional information for the dish based on the individual ingredients, the masses and/or weights of the ingredients added to the dish, nutritional information stored on the client computing device, nutritional information stored via the external resources, and/or other information.

In some implementations, the nutrition module may be configured such that users can customize what nutritional information to display on a dashboard displayed via the user interface. The nutrition module may be configured such that users can set nutritional goals. The nutrition module may be configured to cause the user interface to notify a user when a dish reaches a nutritional threshold amount (e.g., a maximum number of calories). In some implementations, the nutrition module may be configured such that the nutritional information may be displayed via the user interface as a numerical index. Displaying the nutritional information as a numerical index may make the nutritional information easier to understand (e.g., a numerical index may simplify a nutrition label associated with a dish and/or recipe).

The customization module may be configured to customize the previously stored electronic recipes. The customization module may be configured to customize the previously stored electronic recipes responsive to the masses and/or weights of the individual ingredients added to the dish not matching the target masses of the individual ingredients specified by the previously stored electronic recipe. The customization module may be configured to customize a given electronic recipe to reflect the actual masses of the individual ingredients added to the dish during preparation. In some implementations, the customization module may be configured to customize an electronic recipe based on user input via the user interface. For example, a user may specify that the recipe should be scaled (e.g., doubled, halved, etc.). The customization module may be configured to adjust the masses and/or weights of each ingredient in the recipe based on the user input. In some implementations, a user may specify that a specific ingredient should not be used. The customization module may adjust the masses and/or weights of the other ingredients in the recipe, add new ingredients, remove additional ingredients, and/or make other changes to the recipe based on the user specification.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
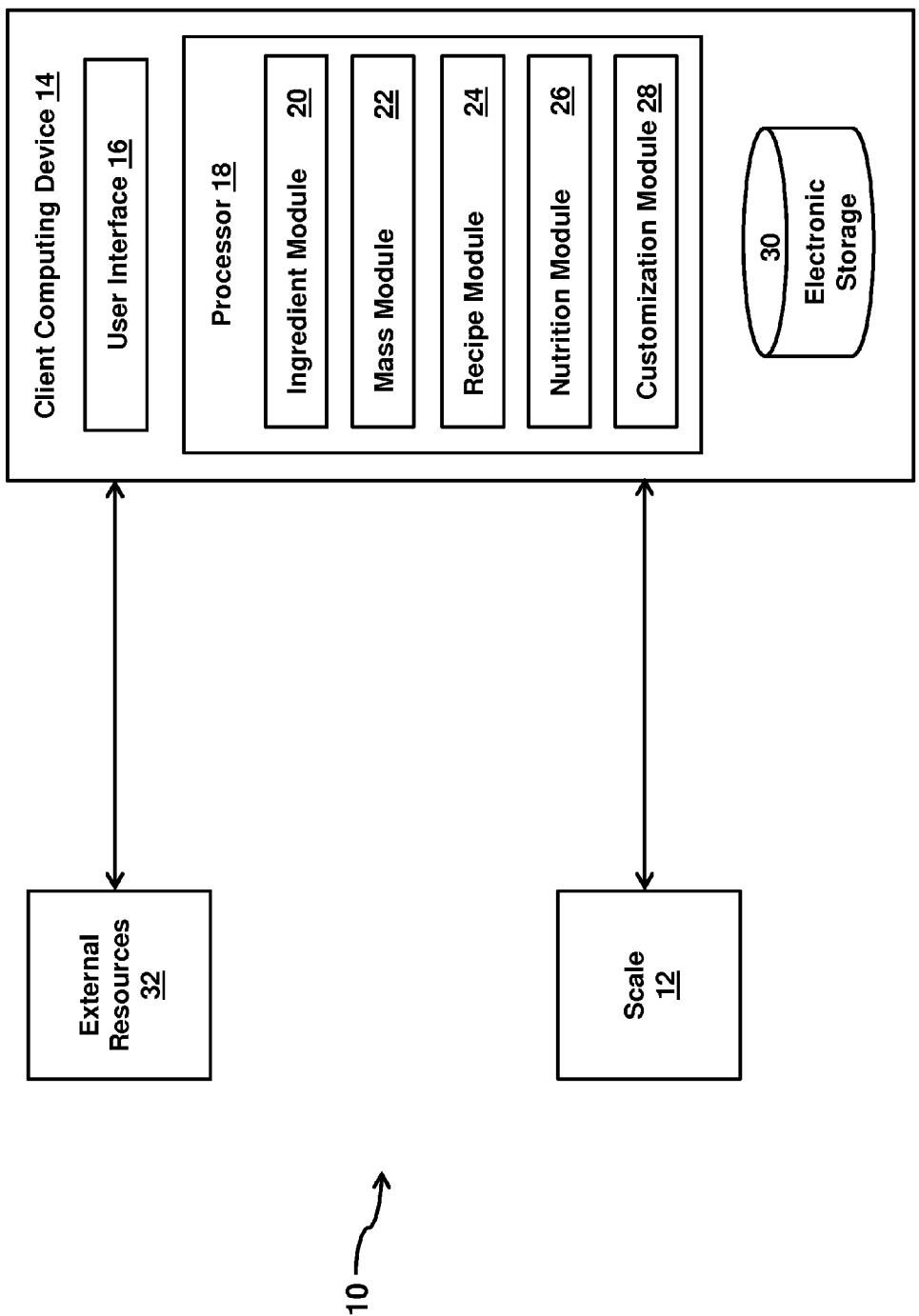
FIG. 1 illustrates a system configured to determine masses, weights, and/or other quantities of individual ingredients added to a food dish during preparation.

FIG. 1 illustrates a system 10 configured to determine masses, weights, and/or other quantities of individual ingredients added to a food dish during preparation. At least some of the components of system 10 may be configured to be used in a food preparation area (e.g., a kitchen). System 10 may include a scale 12, a client computing device 14, external resources 32, and/or other components. System 10 may be configured to weigh individual ingredients of the dish as the ingredients are added to the dish. System 10 may be configured to determine the individual mass and/or weight of each ingredient based on the masses and/or weights of individual ingredients previously added to the dish and/or a current mass and/or weight of the dish as a given ingredient is added.

For example, system 10 may be utilized while preparing a salad. The user may place a bowl and/or other containers on scale 12 and begin to add ingredients of the salad to the bowl. In some implementations, scale 12 may be configured to hold the ingredients without a bowl and/or other containers. In some implementations, system 10 may be configured such that the mass/weight of the bowl may be manually and/or automatically removed from the running weight of a dish measured by scale 12.

The user may indicate which ingredient is being added to the salad via a user interface 16 of client computing device 14. Responsive to the user indicating that a first ingredient (e.g., lettuce) has finished being added to the salad and that a second ingredient (e.g., carrots) will begin to be added to the salad, system 10 may determine a total weight of the first ingredient and begin to determine the weight of the second ingredient. System 10 may determine the weight of the second ingredient as it is added to the salad by, for example, subtracting the total weight of the first ingredient from a current total weight of the salad.

In some implementations, system 10 may be configured to automatically detect than an object (e.g., a bowl, an additional ingredient, etc.) has been placed on scale 12 without any indication from the user. For example, system 10 may determine that a bowl has been placed on scale 12 and automatically tare the scale before a first ingredient is added to a dish.

Responsive to the user finishing preparation of the dish, system 10 may facilitate electronic storage of the individual ingredients, the corresponding masses and/or weights of the individual ingredients in the dish, and/or other information in an electronic recipe. System 10 may be configured to determine nutritional information for the recipe based on the ingredients, the masses and/or weights of the ingredients, and/or other information. The nutritional information may include, for example, information related to calories, vitamins, minerals, and/or nutritional information related to the individual ingredients added to the dish. The electronic recipe may be stored locally on client computing device 14, stored on an external database, shared via social media (e.g., Facebook, Twitter), distributed via email, shared via text message, and/or shared in other ways.

In some implementations, system 10 may be used during preparation of a dish according to an existing electronic recipe. System 10 may be configured such that a user may enter and/or select the existing electronic recipe for preparation. The existing electronic recipe may be stored locally on client computing device 14, stored in an external database, accessed via the internet and/or other networks, and/or be retrieved from other sources. System 10 may be configured to prompt a user to cease adding individual ingredients to the dish during preparation of the existing electronic recipe. The prompts may be based on current masses and/or weights of the ingredients added to the dish during preparation, target masses and/or weights of the individual ingredients specified in the electronic recipe, and/or other information. Responsive to the mass and/or weight of a given ingredient reaching a corresponding target mass and/or weight, user interface 16 may be controlled to prompt the user to cease adding the given ingredient to the dish.

In some implementations, system 10 may be configured to customize the existing electronic recipe entered and/or selected by the user. Responsive to the user adding more and/or less of one or more ingredients than the amounts specified by the existing electronic recipe, system 10 may customize the existing electronic recipe to reflect the actual masses and/or weights of the individual ingredients added to the dish. System 10 may facilitate electronic storage and/or sharing of the customized recipe.

Scale 12 may be configured to generate output signals conveying information related to the masses and/or weights of the individual ingredients added to the dish. Scale 12 may be located in and/or near a food preparation area. A food preparation area may include a kitchen, a countertop, a table, a food specific (e.g., no nuts) preparation surface on a countertop and/or table, and/or other food preparation areas. As such, scale 12 may include surfaces configured to be wiped off and/or cleaned, touch sensitive and/or physical buttons that may be utilized by a user whose finger may be dirtied by food preparation, and/or other features of a scale designed for use in a food preparation area. In some implementations, the whole surface area of scale 12 may be touch sensitive. In some implementations, scale 12 may be portable such that a user may move scale 12 from one food preparation area to another and/or move scale 12 within a food preparation area. Scale 12 may be powered via AC power (e.g., a typical three-prong power outlet), powered via batteries, and/or powered via other sources. In some implementations, scale 12 may be controlled via client computing device 14. As described above, the individual ingredients may include, for example, a first ingredient (e.g., lettuce), a second ingredient (e.g., carrots), and/or additional ingredients. The second ingredient and/or any other additional ingredients may be added successively to the dish after the first ingredient.

In some implementations, a bowl and/or other preparation tools (e.g., a plate, a cup, a tray) may be placed on the scale to hold the individual ingredients as they are added to the dish. In some implementations, scale 12 is configured to receive, hold, and weigh the individual ingredients without additional preparation tools.

Figure 2:
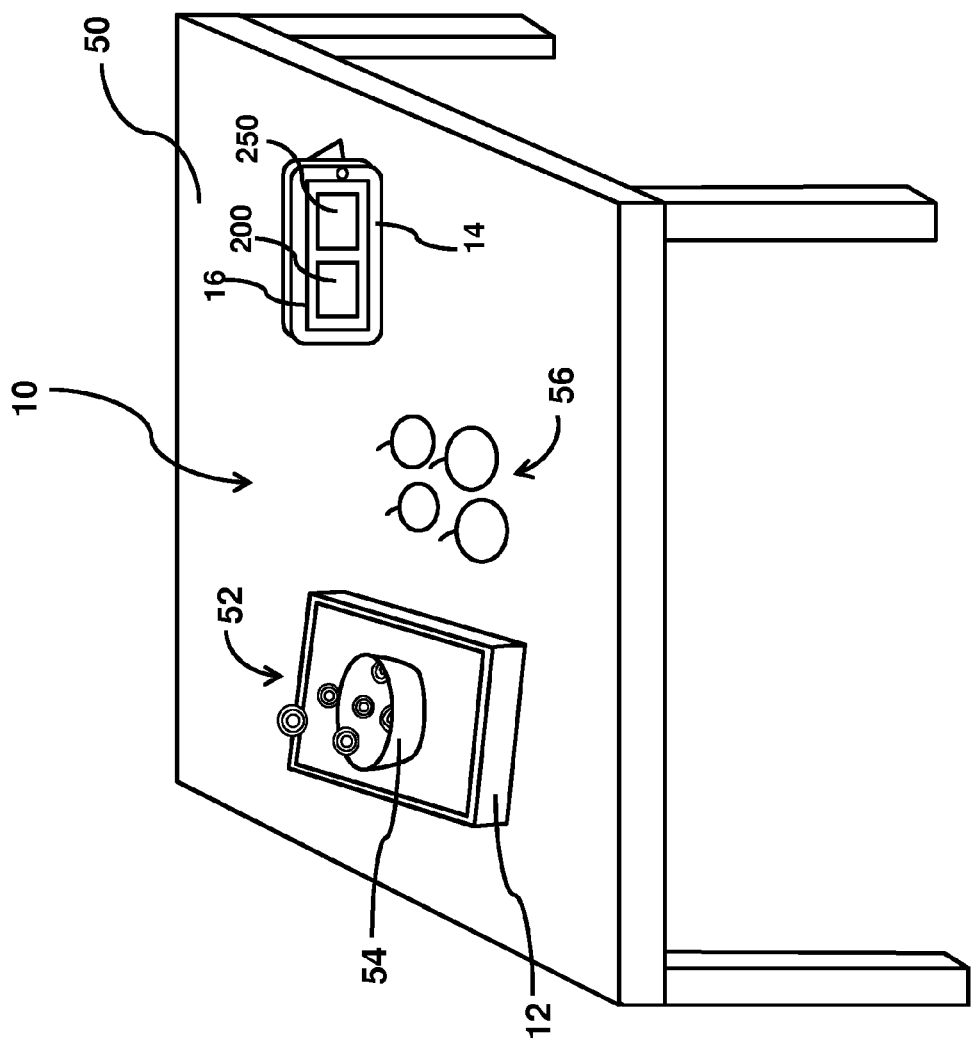
FIG. 2 illustrates a scale on a table during preparation of a dish.

By way of a non-limiting example, FIG. 2 illustrates scale 12 on a table 50 during preparation of a dish. Client computing device 14 is located on table 50 near scale 12. A first ingredient 52 (e.g., onions) has been sliced and placed into bowl 54 on scale 12. A second ingredient 56 (e.g., tomatoes) is on table 50 waiting to be cut and placed into bowl 54. In the example shown in FIG. 2, scale 12 is battery powered. Scale 12 and client computing device 14 communicate wirelessly. The user may indicate via user interface 16 that first ingredient 52 is being added to bowl 54 and then indicate that second ingredient 56 is being placed into bowl 54. User interface 16 may display the weights of the individual ingredients to the user as the individual ingredients are added to bowl 54 on scale 12.

Returning to FIG. 1, it should be noted that the use of terms such as "mass", "weight", and/or other terms related to an amount of the individual ingredients throughout the present disclosure is not intended to be limiting. In some implementations, scale 12 may be configured to generate output signals related to a volume, a physical form (e.g., a bushel and/or an ear of corn), and/or other measures of the individual ingredients added to a dish.

Client computing device 14 may be configured such that a user may access system 10 via client computing device 14. Client computing device 14 may include user interface 16, one or more processors 18, electronic storage 30, and/or other components. In some implementations, client computing device 14 may be configured to communicate with one or more external resources 32 according to a client/server architecture. By way of non-limiting example, a given client computing device 14 may include one or more of a desktop computer, a laptop computer, a handheld computer, a tablet computing platform, a NetBook, a smartphone, and/or other computing platforms.

In some implementations, client computing device 14 may be configured to communicate with scale 12 according to a peer-to-peer architecture, a client/server architecture, and/or other architectures. Client computing device 14 and/or scale 12 may include communication lines, or ports to enable the exchange of information with a network, other computing platforms (e.g., one or more other client computing devices 14), and/or other devices. In some implementations, communication between client computing device 14, scale 12, external resources 32, and/or other components of system 10 may be wireless and/or via wires. For example, client computing device 14 may communicate with scale 12 wirelessly via a Wi-Fi network, via Bluetooth® technology, and/or other wireless technology. In some implementations, client computing device 14 may communicate with scale 12 via a wired USB connection, for example.

User interface 16 may be configured to receive entry and/or selection of ingredient information indicating which individual ingredient is currently being added to the dish during preparation. For example, the ingredient information may indicate whether the first ingredient, the second ingredient, and/or other ingredients are being added to the dish. Receiving entry and/or selection of ingredient information may include a user typing the name of an ingredient via a key pad and/or a keyboard, selecting (e.g., via a mouse and/or a touchscreen) an ingredient from a list of ingredients, selecting a picture of an ingredient, and/or other entry and/or selection. In some implementations, user interface 16 and/or external resources 32 may be configured such that receiving entry and/or selection of the ingredient information may include reading, scanning, and/or optically recognizing information that identifies an individual ingredient. For example, external resources 32 and/or client computing device 14 may include a scanner controlled via user interface 16 that are configured to recognize a bar code and/or other identifying information included on the packaging of an individual ingredient. External resources 32 and/or client computing device 14 may include optical recognition equipment controlled via user interface 16 that is configured to optically recognize individual ingredients.

In some implementations, user interface 16 may be configured to receive entry and/or selection of an electronic recipe for preparation by the user. The electronic recipe may specify target masses and/or weights of the individual ingredients in the dish. For example, the electronic recipe may specify a first target mass for the first ingredient and a second target mass for the second ingredient. The existing electronic recipe may be stored locally on client computing device 14, stored in an external database, accessed via the internet and/or other networks, and/or be retrieved from other sources. User interface 16 may be configured such that a user may navigate through electronic folders, the internet, and/or other electronic storage areas to locate, view, and/or select a desired recipe.

User interface 16 may be configured to provide an interface between client computing device 14 and the user through which the user may provide information to and receive information from system 10. This enables data, cues, results, and/or instructions and any other communicable items, collectively referred to as "information," to be communicated between the user and system 10.

Examples of interface devices suitable for inclusion in user interface 16 include a touch screen, a keypad, touch sensitive and/or physical buttons, switches, a keyboard, knobs, levers, a display, speakers, a microphone, an indicator light, an audible alarm, a printer, and/or other interface devices. In some implementations, user interface 16 includes a plurality of separate interfaces. In some implementations, user interface 16 includes at least one interface that is provided integrally with client computing device 14.

It is to be understood that other communication techniques, either hard-wired or wireless, are also contemplated by the present disclosure as user interface 16. For example, the present disclosure contemplates that user interface 16 may be integrated with a removable storage interface provided by client computing device 14. In this example, information may be loaded into client computing device 14 from removable storage (e.g., a smart card, a flash drive, a removable disk) that enables the user to customize the implementation of client computing device 14. Other exemplary input devices and techniques adapted for use with client computing device 14 as user interface 16 include, but are not limited to, an RS-232 port, RF link, an IR link, modem (telephone, cable or other). In short, any technique for communicating information with client computing device 14 is contemplated by the present disclosure as user interface 16.

Processor 18 may be configured to execute computer program modules. The computer program modules may be configured to enable an expert and/or user associated with a given client computing device 14 to interface with scale 12 and/or external resources 32, and/or provide other functionality attributed herein to client computing device 14. The computer program modules may include an ingredient module 20, a mass module 22, a recipe module 24, a nutrition module 26, a customization module 28, and/or other modules.

Ingredient module 20 may be configured to obtain ingredient information indicating which individual ingredient is currently being added to the dish. The ingredient information may be obtained from a user via user interface 16, obtained via external resources 32, and/or obtained via in other ways. For example, the ingredient information may indicate whether the first ingredient, the second ingredient, and/or other ingredients are being added to the dish. Ingredient module 20 may be configured to obtain the ingredient information by causing user interface 16 to display one or more views of a graphical user interface to a user. The one or more views may include selectable images, a textual information entry field, and/or other information that facilitates entry and/or selection of ingredient information by the user. For example, ingredient module 20 may cause user interface 16 to display selectable pictures of various ingredients. Responsive to the user selecting one of the displayed pictures, ingredient module 20 may obtain ingredient information indicating that the ingredient displayed in the selected picture is being added to the dish. As another example, ingredient module 20 may obtain ingredient information that corresponds to the name of an ingredient typed by a user into the textual information entry field.

Figure 2A:
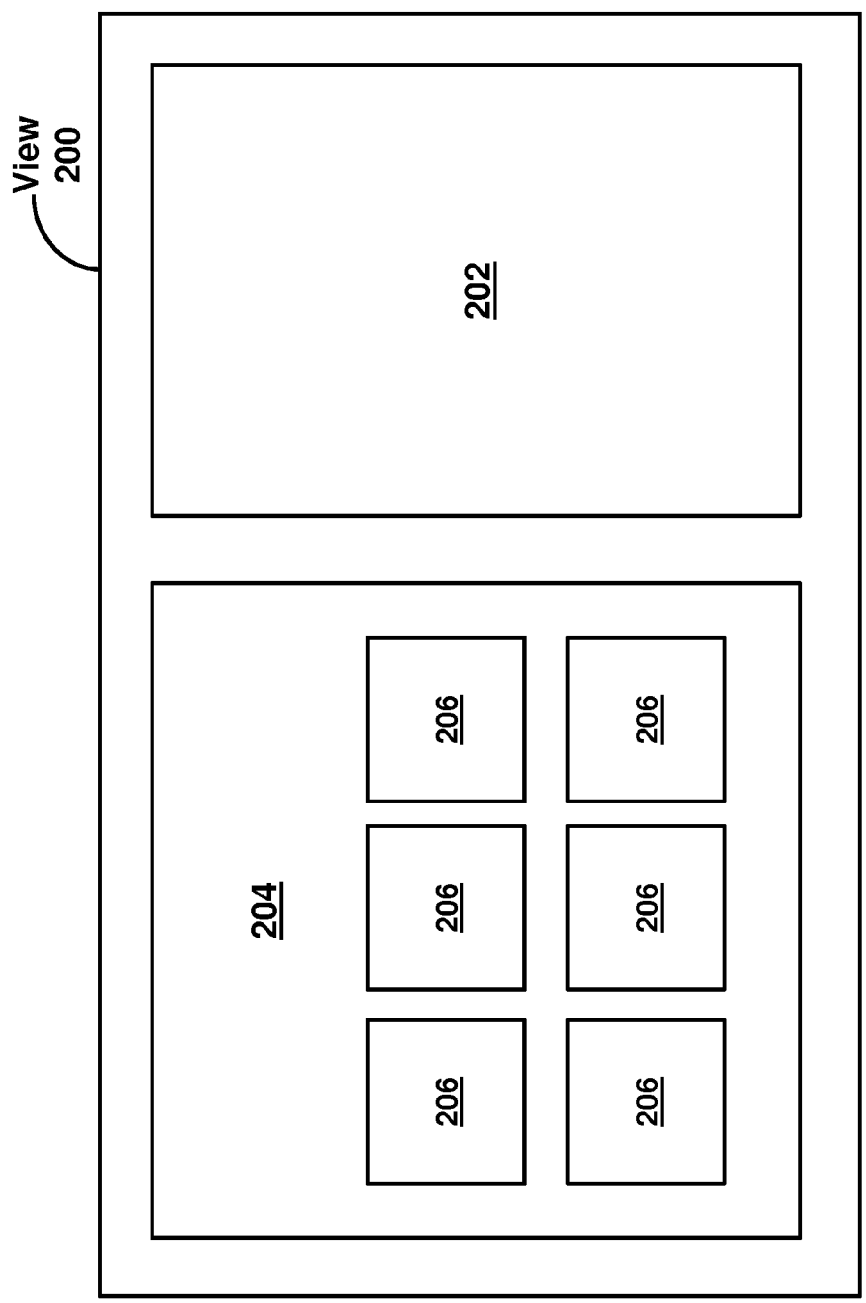
FIG. 2A illustrates a view of a graphical user interface displayed to a user by a user interface that facilitates entry and/or selection of ingredient information by a user.

FIG. 2A illustrates a view 200 of a graphical user interface displayed to a user by user interface 16 (not shown in FIG. 2A) that facilitates entry and/or selection of ingredient information by the user. View 200 may be presented to a user in the food preparation area via client computing device 14 (as shown in FIG. 2), for example. In some implementations, view 200 may include a textual information entry field 202, a visual information field 204, and/or other fields.

In some implementations, textual information entry field 202 may be configured such that a user may type the name of an ingredient and/or information related to an ingredient into field 202 via user interface 16. Visual information field 204 may include individual images 206 of possible ingredients for selection by the user and/or other information. The individual images may be associated with ingredients in a list of possible ingredients stored in external databases that are part of external resources 32, for example. In some implementations, the name of the ingredient typed into field 202 may be the ingredient information. In some implementations, ingredient module 20 may be configured to obtain the ingredient information via a search of the external databases for ingredients that correspond to the ingredient information entered into field 202 and/or the ingredients associated with the images selected from field 204.

The description of the information presented by the different fields 202 and/or 204 described herein is for illustrative purposes, and is not intended to be limiting, as any of fields 202, 204, and/or other fields may provide more or less information than is described. For example, one or more of fields 202 and/or 204 may be eliminated, and some or all of its information may be provided by other ones of fields 202, 204, and/or other fields not shown in FIG. 2A.

Returning to FIG. 1, in some implementations, ingredient module 20 may be configured such that obtaining the ingredient information via external resources 32 may include reading, scanning, and/or optically recognizing information that identifies an individual ingredient. For example, external resources 32 may include a scanner configured to recognize a bar code and/or other identifying information included on the packaging of an individual ingredient. In some implementations, obtaining the ingredient information via external resources 32 may include sensing presence of an individual ingredient on or near scale 12, client computing device 14, and/or other components of system 10. For example, external resources 32 may include one or more sensors configured to detect presence of radio frequency identification (RFID) tags in the packaging of an ingredient and/or other sensors configured to detect presence of other markers in the individual ingredients themselves.

Mass module 22 may be configured to determine the masses and/or weights of the individual ingredients added to the dish. The determinations may be based on the output signals from scale 12. The mass and/or weight determinations for the individual ingredients may be made by mass module 22 without intervention via scale 12 and/or client computing device 14 by the user. For example, the user does not need to manually tare scale 12 after adding a first ingredient and before adding a second ingredient. The mass and/or weight determinations for the individual ingredients may be made with the previously added ingredients still on scale 12 as a current ingredient is being added to the dish. For example, responsive to the obtained ingredient information indicating that the first ingredient is being added to the dish, mass module 22 may determine a first mass and/or weight of the first ingredient. Responsive to the obtained ingredient information indicating that the second ingredient is being added to the dish (e.g., with the first ingredient still on scale 12), mass module 22 may determine a second mass and/or weight of the second ingredient. The second mass and/or weight of the second ingredient may be based on the first mass of the first ingredient and a total mass of the dish.

In some implementations, mass module 22 may be configured such that determining the second mass and/or weight of the second ingredient based on the first mass and/or weight of the first ingredient and a total mass and/or weight of the dish includes determining a mass and/or weight of the second ingredient by subtracting a total mass and/or weight of the first ingredient from a total mass and/or weight of the dish. In some implementations, mass module 22 may be configured to tare scale 12 before each individual ingredient is added to the dish. For example, mass module 22 may be configured to tare scale 12 before the first individual ingredient is added to the dish and before the second individual ingredient is added to the dish. In some implementations, mass module 22 may be configured such that the masses and/or weights of the individual ingredients are current running totals of the masses and/or weights of the individual ingredients added to the dish during preparation.

Recipe module 24 may be configured to facilitate electronic storage of the individual ingredients and/or the corresponding masses and/or weights of the individual ingredients added to the dish in an electronic recipe. The electronic recipe may be stored locally on client computing device 14, stored remotely via external resources 32 (e.g., in an electronic recipe data base stored on an external server), stored in a third party application (e.g., Evernote), stored in a proprietary format, and/or stored in other locations. In some implementations, information related to the stored electronic recipe may be used for data aggregation. In some implementations, recipe module 24 may be configured to facilitate sharing of the electronic recipe via social media (e.g., Facebook, Twitter), distribution of the electronic recipe via email, posting of the electronic recipe to a blog and/or other websites, sharing of the electronic recipe via text message, and/or sharing in other ways. For example, a chef may utilize system 10 while experimenting with one or more new dishes. Recipe module 24 may facilitate electronic storage of the ingredients and corresponding masses and/or weights of the ingredients in each new dish as a series of electronic recipes. Recipe module 24 may facilitate posting one or more of the newly stored recipes on a blog associated with the chef.

In some implementations, recipe module 24 may be configured such that the electronic recipe may be edited by a user before storage and/or sharing. Editing may include editing text, adding photos and/or video, adding web links, directly integrating the electronic recipe with other applications (e.g., Instagram, Pinterest, etc.), and/or other customization.

In some implementations, recipe module 24 may be configured such that the electronic recipe may include pictures of the dish, videos of the dish and/or preparation of the dish, and/or other information. In some implementations, recipe module 24 may facilitate uploading of pictures, videos, and/or other information via user interface 16. In some implementations, the electronic recipes may be stored with a standard format. The standard format may make it easier for a user to view a previously stored recipe during dish preparation, for example.

In some implementations, recipe module 24 may be configured to facilitate entry, selection, viewing, and/or following of previously stored electronic recipes via user interface 16. Facilitating the following of a previously stored electronic recipe may include facilitating a step-by-step progression through recipe preparation. In some implementations, the previously stored electronic recipes may be generated via system 10 as described above. In some implementations, the previously stored electronic recipes may include electronic recipes generated by other methods, electronic recipes stored in external databases (e.g., external resources 32), recipes stored locally on client computing device 14, recipes accessed via a network (e.g., the internet), and/or other recipes. The electronic recipes may specify target masses and/or weights of individual ingredients in a dish. For example, a given electronic recipe may specify a first target mass and/or weight for a first ingredient and/or a second target mass and/or weight for a second ingredient. Recipe module 24 may be configured to cause user interface 16 to display a selected electronic recipe to a user while the user is adding ingredients to a dish according to the displayed recipe.

In some implementations, recipe module 24 may be configured to, responsive to the masses and/or weights of the individual ingredients added to the dish reaching the target masses and/or weights of the individual ingredients specified by the recipe (the masses and/or weights being determined as described herein), control user interface 16 to prompt the user to cease adding the individual ingredients. For example, responsive to the mass and/or weight of the first ingredient reaching the first target mass and/or weight of the first ingredient, recipe module 24 may control user interface 16 to prompt the user to cease adding the first ingredient. Responsive to the mass and/or weight of the second ingredient reaching the second target mass and/or weight of the second ingredient, recipe module 24 may control user interface 16 to prompt the user to cease adding the second ingredient. As described above, the mass and/or weight of the second ingredient may be determined based on the mass and/or weight of the first ingredient and a total mass and/or weight of the dish. Prompting the user may include, for example, displaying a visual message via user interface 16, sounding an audible alarm via client computing device 14, and/or other prompts.

Figure 2B:
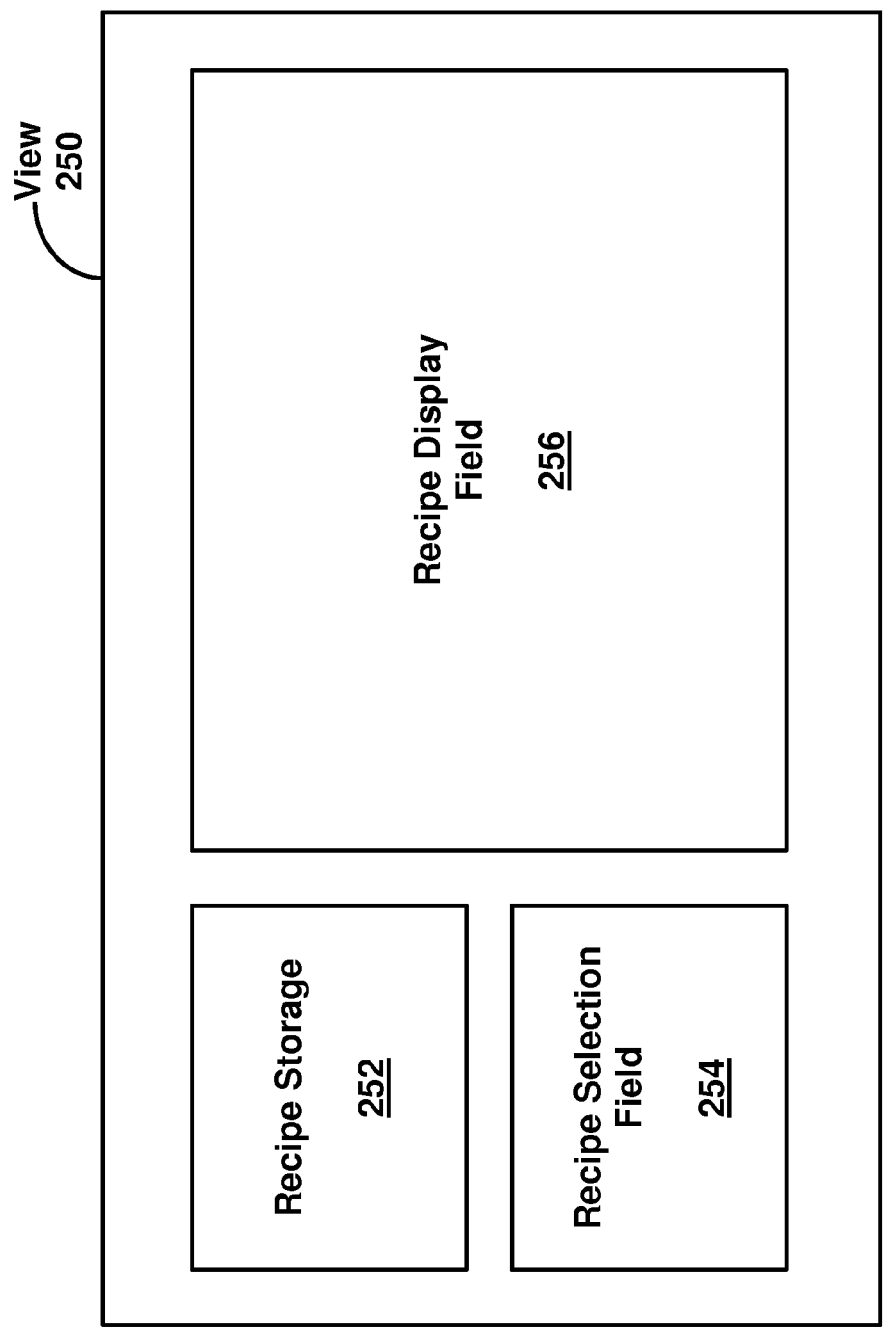
FIG. 2B illustrates a view of a graphical user interface displayed to a user by a user interface that facilitates electronic storage of recipes; entry, selection, viewing, and/or following of previously stored electronic recipes; nutritional information associated with a recipe; and/or a dashboard.

In some implementations, recipe module 24 may be configured to facilitate electronic storage of the recipes by causing user interface 16 to display one or more views of the graphical user interface to a user. Recipe module 24 may be configured to facilitate entry, selection, viewing, and/or following of previously stored electronic recipes via the graphical user interface and/or the one or more views. FIG. 2B illustrates a view 250 of a graphical user interface displayed to a user by user interface 16 (not shown in FIG. 2B) that facilitates electronic storage of recipes; entry, selection, viewing, and/or following of previously stored electronic recipes; nutritional information associated with a recipe; and/or a dashboard. View 250 may be presented to a user in a food preparation area via client computing device 14 (as shown in FIG. 2), for example. In some implementations, view 250 may include a recipe storage field 252, a recipe selection field 254, a recipe display field 256, and/or other fields.

In some implementations, recipe storage field 252 may be configured such that a user may select a recipe for electronic storage, enter a title name for recipe to be stored, enter a textual summary of the recipe, add images, add video, select a storage location and/or perform other actions related to storing the recipe. Recipe selection field 254 may be configured to allow a user to electronically navigate to a desired recipe, select the desired recipe, search for a recipe by entering a textual description of the recipe, and/or perform other actions related to selection of a desired recipe.

Recipe display field 256 may be configured to display a selected recipe to a user. The recipe may displayed such that all of the recipe steps are visible in field 256 at the same time, such that one recipe step is displayed at a time, and/or some combination thereof. Recipe field 256 and/or user interface 16 may be configured such that a user may navigate from recipe step to recipe step by way of a sliding gesture on user interface 16 in field 256, for example. Field 256 may be configured to display images, video, and/or other information related to the selected recipe. Field 256 may be configured to be controlled to prompt the user to cease adding an ingredient to a dish as described herein. In some implementations, recipe display field 256 may display nutritional information associated with the recipe. In some implementations, recipe display field 256 and/or view 250 as a whole may present a dashboard to a user. The dashboard may present a summary and/or overview of an electronic recipe, progression through preparation of an electronic recipe, and/or other information.

The description of the information presented by the different fields 252, 254, and/or 256 described herein is for illustrative purposes, and is not intended to be limiting, as any of fields 252, 254, 256, and/or other fields may provide more or less information than is described. For example, one or more of fields 252, 254, and/or 256 may be eliminated, and some or all of its information may be provided by other ones of fields 252, 254, 256, and/or other fields not shown in FIG. 2B.

Returning to FIG. 1, nutrition module 26 may be configured to determine nutritional information for the dish. Nutrition module 26 may be configured to determine nutritional information for the dish based on the individual ingredients, the masses and/or weights of the ingredients added to the dish, nutritional information stored on client computing device 14, nutritional information stored via external resources 32, and/or other information. In some implementations, external resources 32 may include a nutritional information database accessed by nutrition module 26 to determine the nutritional information. The nutritional information may include, for example, information related to calories, vitamins, minerals, a nutritional index, a nutritional summary, nutritional goals, an analysis of the nutritional information, a proprietary format, and/or other nutritional information related to the individual ingredients added to the dish. Nutrition module 26 may associate the determined nutritional information with a corresponding recipe for the dish stored by recipe module 24. In some implementations, the electronic recipe and the associated nutritional information may be stored in the same electronic file. For example, a future user may view the nutritional information of a stored electronic recipe and decide whether or not to prepare the dish based on the nutritional information. In some implementations, nutrition module 26 may be configured to facilitate presentation of the nutritional information for a given recipe via user interface 16.

In some implementations, the nutritional information may include information related to specific dietary labels, allergens, and/or other information. The allergens may include, for example, foods such as dairy, shellfish, tree nuts, peanuts, and/or other food and/or drink allergens. The specific dietary labels may include vegetarian, vegan, gluten free, kosher, and/or other dietary labels. In some implementations, nutrition module 26 may determine the information related to specific dietary labels, allergens, and/or other information so that a user may be notified of the specific dietary labels and/or allergens associated with a given recipe prior to preparing the dish. In some implementations, nutrition module 26 may determine the information related to specific dietary labels, allergens, and/or other information so that recipes may be sorted according to their associated dietary labels, allergens, and/or other information. In some implementations, nutrition module 26 may cause user interface 16 to alert a user of specific information related to allergens and/or dietary labels responsive to the user viewing a given recipe via user interface 16.

For example, nutrition module 26 may determine that one or more of the individual ingredients added to the dish (e.g., peanut oil) and then stored in an electronic recipe are known allergens. Nutrition module 26 may cause user interface 16 to alert the user to the known allergen when the user views the electronic recipe. As another example, a user may sort recipes stored in an external recipe database (e.g., external resources 32) to find gluten free dishes based on nutritional information previously determined by nutrition module 26 and stored with the recipes in the database.

In some implementations, nutrition module 26 may be configured such that users can customize what nutritional information to display on a dashboard displayed via a user interface 16. Nutrition module 26 may be configured such that users can set nutritional goals. Nutrition module 26 may be configured to cause user interface 16 to notify a user when a dish reaches a nutritional threshold amount (e.g., a maximum number of calories). In some implementations, nutrition module 26 may be configured such that the nutritional information may be displayed via user interface 16 as a numerical index. Displaying the nutritional information as a numerical index may make the nutritional information easier to understand (e.g., a numerical index may simplify a nutrition label associated with a dish and/or recipe).

Customization module 28 may be configured to customize the previously stored electronic recipes. Customization module 28 may be configured to customize the previously stored electronic recipes responsive to the masses and/or weights of the individual ingredients added to the dish not matching the target masses of the individual ingredients specified by the previously stored electronic recipe. Customization module 28 may be configured to customize a given electronic (e.g., previously stored via recipe module 24, accessed via the internet, etc.) recipe to reflect the actual masses of the individual ingredients added to the dish during preparation.

In some implementations, customization module 28 may be configured to facilitate electronic storage of the customized electronic recipe. The customized electronic recipe may be stored locally on client computing device 14, stored remotely via external resources 32 (e.g., in an electronic recipe data base stored on an external server), and/or stored in other locations. In some implementations, customization module 28 may be configured to facilitate sharing of the electronic recipe via social media (e.g., Facebook, Twitter), distribution of the electronic recipe via email, posting of the electronic recipe to a blog and/or other websites, sharing of the electronic recipe via text message, and/or sharing in other ways. In some implementations, customization module 28 may be configured to associate the customized recipe with the previously stored electronic recipe.

For example, a second user may select a first user's previously stored electronic recipe for preparation (e.g., facilitated by recipe module 24). The second user may begin adding the first ingredient until the weight of the first ingredient (e.g., determined via scale 12 and/or mass module 22) reaches the target weight for that ingredient and the user is prompted to cease adding the first ingredient (e.g., via user interface 16 and/or recipe module 24). The user may then add the second ingredient to the dish but cease adding the ingredient before being prompted to do so. The user may add a third ingredient to the dish in an amount that exceeds the target in the recipe (even though system 10 may have prompted the user to cease adding the third ingredient when the target was reached). Customization module 28 may be configured to facilitate electronic storage of the customized electronic recipe that reflects the actual amounts of the ingredients added to the dish. Customization module 28 may be configured to associated the customized recipe with the previously stored electronic recipe by, for example, changing a filename of the electronic recipe to reflect the name of the first user and the name of the second user (e.g., user two's version of user one's salad).

In some implementations, customization module 28 may be configured to customize an electronic recipe based on user input via user interface 16. For example, a user may specify that the recipe should be scaled (e.g., doubled, halved, etc.). Customization module 28 may be configured to adjust the masses and/or weights of each ingredient in the recipe based on the user input. In some implementations, a user may specify that a specific ingredient should not be used. Customization module 28 may adjust the masses and/or weights of the other ingredients in the recipe, add new ingredients, remove additional ingredients, and/or make other changes to the recipe based on the user specification.

Electronic storage 30 may comprise electronic storage media that electronically stores information. The electronic storage media of electronic storage 30 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 30 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 30 may store software algorithms, information (e.g., an electronic recipe) determined by processor 18, and/or other information that enables system 10 to function properly. Electronic storage 30 may be (in whole or in part) a separate component within system 10, or electronic storage 30 may be provided (in whole or in part) integrally with one or more other components of system 10 (e.g., client computing device 14, processor 18).

External resources 32 may include sources of information (e.g., an electronic recipe database, a nutritional information database), one or more servers outside of system 10 (e.g., one or more servers associated with a social network), a network (e.g., the internet), electronic storage, equipment related to Wi-Fi technology, equipment related to Bluetooth® technology, data entry devices, scanning equipment, sensors, and/or other resources. External resources 32 may include optical recognition equipment configured to optically recognize individual ingredients. In some implementations, some or all of the functionality attributed herein to external resources 32 may be provided by resources included in system 10. External resources 32 may be configured to communicate with client computing device 14 and/or other components of system 10 via wired and/or wireless connections, via a network (e.g., a local area network and/or the internet), via cellular technology, via Wi-Fi technology, and/or via other resources. For example, recipe module 24 may access an electronic recipe database that is part of external resources 32 via the internet. As another example, a bar code scanner that is part of external resources 32 may communicate with client computing device 14 via a removable wired connection (e.g., a USB connection).

Processor 18 may be configured to provide information processing capabilities in system 10. As such, processor 18 may comprise one or more of a digital processor, an analog processor, a digital circuit designed to process information, an analog circuit designed to process information, a state machine, and/or other mechanisms for electronically processing information. Although processor 18 is shown in FIG. 1 as a single entity, this is for illustrative purposes only. In some implementations, processor 18 may comprise a plurality of processing units. These processing units may be physically located within the same device (e.g., client computing device 14), or processor 18 may represent processing functionality of a plurality of devices operating in coordination (e.g., client computing device 14 and scale 12). Processor 18 may be configured to execute modules 20, 22, 24, 26, and/or 28 by software; hardware; firmware; some combination of software, hardware, and/or firmware; and/or other mechanisms for configuring processing capabilities on processor 18.

It should be appreciated that although modules 20, 22, 24, 26, and 28 are illustrated in FIG. 1 as being co-located within a single processing unit, in implementations in which processor 18 comprises multiple processing units, one or more of modules 20, 22, 24, 26, and/or 28 may be located remotely from the other modules (e.g., such as within scale 12). The description of the functionality provided by the different modules 20, 22, 24, 26, and/or 28 described herein is for illustrative purposes, and is not intended to be limiting, as any of modules 20, 22, 24, 26, and/or 28 may provide more or less functionality than is described. For example, one or more of modules 20, 22, 24, 26, and/or 28 may be eliminated, and some or all of its functionality may be provided by other modules 20, 22, 24, 26, and/or 28. As another example, processor 18 may be configured to execute one or more additional modules that may perform some or all of the functionality attributed below to one of modules 20, 22, 24, 26, and/or 28. In some implementations, one or more of modules 20, 22, 24, 26, and/or 28 may be executed by a processor incorporated in scale 12, external resources 32, and/or other components of system 10.

Figure 3:
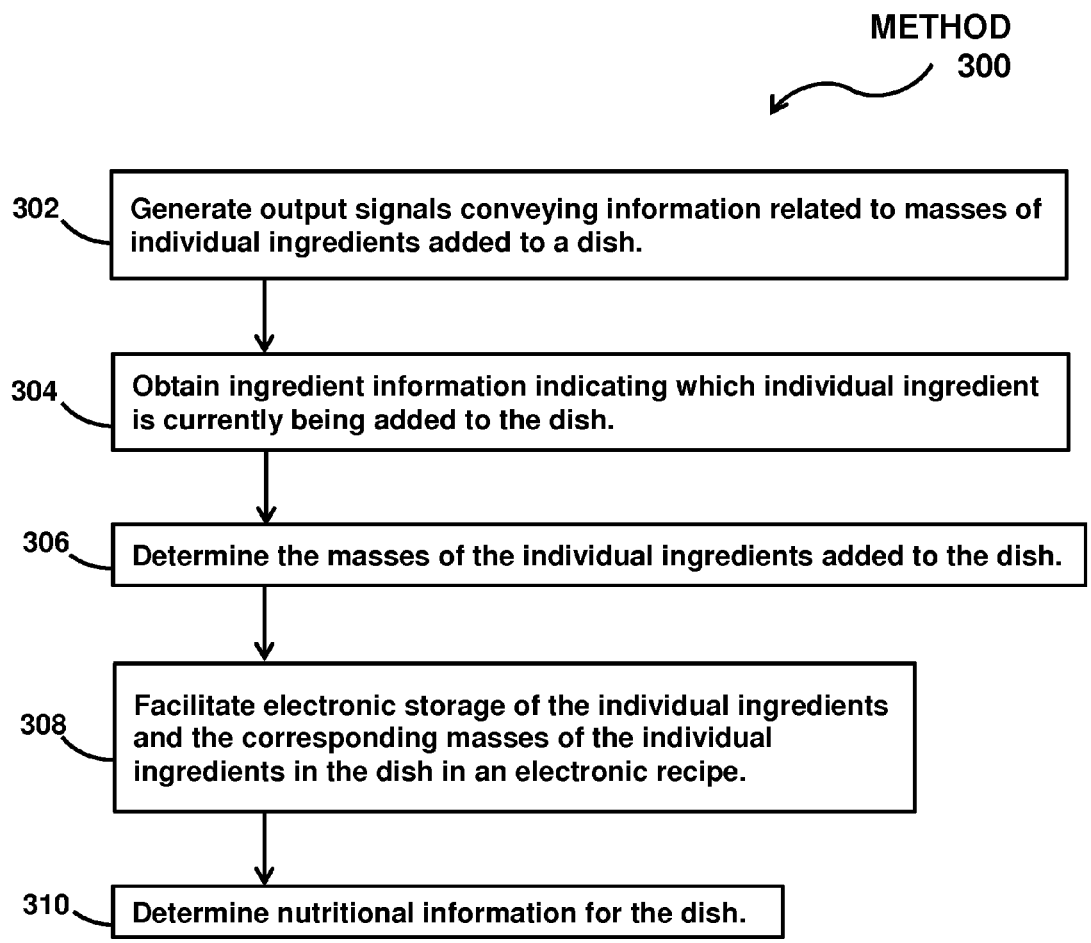
FIG. 3 illustrates a method for determining masses of individual ingredients added to a dish during preparation.
Figure 4:
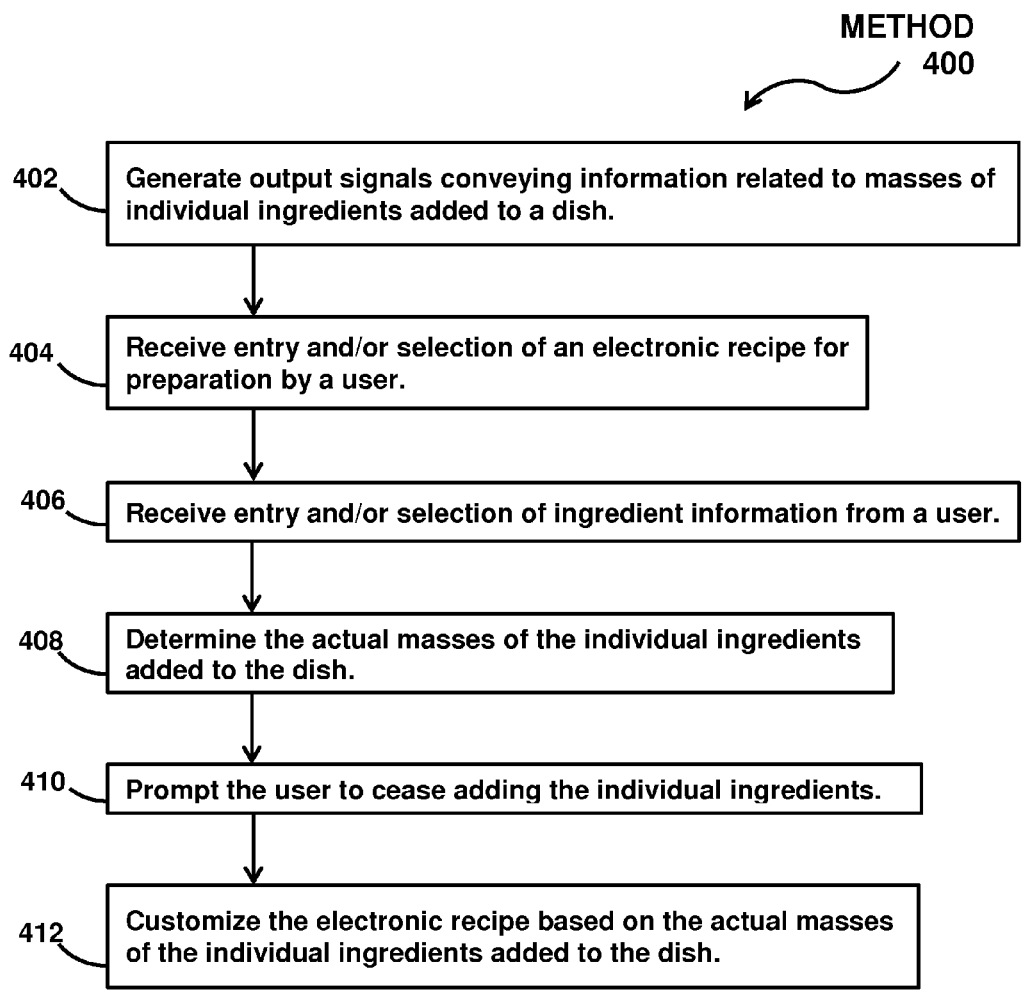
FIG. 4 illustrates a method for prompting a user to cease adding individual ingredients to a dish during preparation.

FIG. 3 illustrates a method 300 for determining masses of individual ingredients added to a dish during preparation. FIG. 4 illustrates a method 400 for prompting a user to cease adding individual ingredients to a dish during preparation. The operations of method 300 and/or 400 presented below are intended to be illustrative. In some implementations, method 300 and/or 400 may be accomplished with one or more additional operations not described, and/or without one or more of the operations discussed. Additionally, the order in which the operations of method 300 and/or 400 are respectively illustrated in FIG. 3 and/or FIG. 4 and described below is not intended to be limiting.

In some implementations, method 300 and/or 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 and/or 400 in response to instructions stored electronically on an electronic storage medium. The one or more processing devices may include one or more devices configured through hardware, firmware, and/or software to be specifically designed for execution of one or more of the operations of method 300 and/or 400.

Referring to FIG. 3 and method 300, at an operation 302, output signals conveying information related to masses of individual ingredients added to a dish may be generated. The individual ingredients may include, for example, a first ingredient and a second ingredient. The second ingredient may be added to the dish after the first ingredient. Operation 302 may be performed by a scale that is the same as or similar to scale 12 (shown in FIG. 1 and described herein). In some implementations, the scale may receive, hold, and weigh the individual ingredients.

At an operation 304, ingredient information indicating which individual ingredient is currently being added to the dish may be obtained. The ingredient information may be obtained from a user via a user interface. The ingredient information may indicate whether the first ingredient or the second ingredient is being added to the dish. Operation 304 may be performed by a computer program module that is the same as or similar to ingredient module 20 (shown in FIG. 1 and described herein).

At an operation 306, the masses of the individual ingredients added to the dish may be determined. The mass determinations may be based on the output signals. Responsive to the obtained ingredient information indicating that the first ingredient is being added to the dish, a first mass of the first ingredient may be determined. Responsive to the obtained ingredient information indicating that the second ingredient is being added to the dish, a second mass of the second ingredient may be determined. The second mass of the second ingredient may be determined based on the first mass of the first ingredient and a total mass of the dish. In some implementations, the masses of the individual ingredients added to the dish are the weights of the individual ingredients added to the dish. In some implementations, the scale may be tared before the first individual ingredient is added to the dish and/or before the second individual ingredient is added to the dish. In some implementations, the weight of the second ingredient may be determined by subtracting a total weight of the first ingredient from a total weight of the dish. Operation 306 may be performed by a computer program module that is the same as or similar to mass module 22 (shown in FIG. 1 and described herein).

At an operation 308, electronic storage, in the form of an electronic recipe, of the individual ingredients and the corresponding masses may be facilitated. In some implementations, the electronic recipe may be selected, viewed, and followed by a user via the user interface. Operation 308 may be performed by a computer program module that is the same as or similar to recipe module 24 (shown in FIG. 1 and described herein).

At an operation 310, nutritional information for the dish may be determined. The nutritional information may comprise information related to calories, vitamins, minerals, and/or other nutritional elements in the individual ingredients added to the dish. In some implementations, the nutritional information may be presented to a user via the user interface. Operation 310 may be performed by a computer program module that is the same as or similar to nutrition module 26 (shown in FIG. 1 and described herein).

Referring to FIG. 4 and method 400, at an operation 402, output signals conveying information related to actual masses of individual ingredients added to a dish may be generated. The individual ingredients may include, for example, a first ingredient and a second ingredient. The second ingredient may be added to the dish after the first ingredient. Operation 402 may be performed by a scale that is the same as or similar to scale 12 (shown in FIG. 1 and described herein). In some implementations, the scale may receive, hold, and weigh the individual ingredients.

At an operation 404, entry and/or selection of an electronic recipe for preparation by a user may be received. The electronic recipe may specify target masses of the individual ingredients in the dish. For example, the electronic recipe may specify a first target mass for the first ingredient and a second target mass for the second ingredient. Operation 404 may be performed by a user interface that is the same as or similar to user interface 16 (shown in FIG. 1 and described herein).

At an operation 406, entry and/or selection of ingredient information may be received from a user. The ingredient information may indicate which individual ingredient is currently being added to the dish during preparation. For example, the ingredient information may indicate whether the first ingredient or the second ingredient is being added to the dish. Operation 406 may be performed by a user interface that is the same as or similar to user interface 16 (shown in FIG. 1 and described herein).

At an operation 408, the actual masses of the individual ingredients added to the dish may be determined. The actual masses may be determined based on the output signals, and/or other information. The actual masses of the individual ingredients added to the dish may be the weights of the individual ingredients added to the dish. The weights of the individual ingredients may be current running totals of the weights of the individual ingredients added to the dish during preparation. Operation 408 may be performed by a computer program module that is the same as or similar to mass module 22 (shown in FIG. 1 and described herein).

At an operation 410, the user interface may be controlled to prompt the user to cease adding the individual ingredients. The user interface may be controlled to prompt the user to cease adding the individual ingredients responsive to the actual masses of the individual ingredients added to the dish reaching the target masses of the individual ingredients specified by the recipe. For example, responsive to the actual mass of the first ingredient reaching the first target mass of the first ingredient, the user may be prompted to cease adding the first ingredient, remove any excess mass of the ingredient above the first target mass, and/or perform other actions. The user may be prompted to remove excess mass in order to maintain one or more ratios between ingredients specified by a recipe and/or other sources of ratio information. Responsive to the actual mass of the second ingredient reaching the second target mass of the second ingredient, the user may be prompted to cease adding the second ingredient. The actual mass of the second ingredient may be determined based on the actual mass of the first ingredient and a total mass of the dish. Operation 410 may be performed by a computer program module that is the same as or similar to recipe module 24 (shown in FIG. 1 and described herein).

At an operation 412, the electronic recipe may be customized based on the actual masses of the individual ingredients added to the dish. Responsive to the actual masses of the individual ingredients added to the dish not matching the target masses of the individual ingredients specified by the recipe, the electronic recipe may be customized to reflect the actual masses of the individual ingredients added to the dish. In some implementations, the customized recipe may be stored electronically. Operation 412 may be performed by a computer program module that is the same as or similar to user customization module 28 (shown in FIG. 1 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to determine user-created recipes based on indications of individual ingredients added to a dish and determinations of masses of individual ingredients added to the dish during preparation, the system comprising:
   a scale configured to generate output signals conveying information related to the masses of the individual ingredients added to the dish, the individual ingredients including a first ingredient and a second ingredient, the second ingredient being added to the dish after the first ingredient, and
   one or more processors configured by machine-readable instructions to:
      obtain ingredient information indicating which individual ingredient is currently being added to the dish, the ingredient information obtained from a user via a user interface, the ingredient information indicating whether the first ingredient or the second ingredient is being added to the dish;
      determine the masses of the individual ingredients added to the dish, the mass determinations based on the output signals from the scale,
         wherein, responsive to the obtained ingredient information indicating that the first ingredient is being added to the dish, determine a first mass of the first ingredient, and
         responsive to the obtained ingredient information indicating that the second ingredient is being added to the dish, determine a second mass of the second ingredient based on the first mass of the first ingredient and a total mass of the dish; and
      facilitate electronic storage of information that indicates both the individual ingredients and the determined masses of the individual ingredients in the dish in a new electronic recipe, such that information indicating the first ingredient, the first mass of the first ingredient, second ingredient, and the second mass of the second ingredient is stored in the new electronic recipe.

2. The system of claim 1, wherein the scale is configured to receive, hold, and weigh the individual ingredients.

3. The system of claim 2, wherein the masses of the individual ingredients added to the dish are the weights of the individual ingredients added to the dish.

4. The system of claim 2, wherein the one or more processors are further configured by machine-readable instructions to tare the scale before the first individual ingredient is added to the dish and before the second individual ingredient is added to the dish.

5. The system of claim 2, wherein the one or more processors are further configured by machine-readable instructions to determine a weight of the second ingredient by subtracting a total weight of the first ingredient from a total weight of the dish.

6. The system of claim 1, wherein the new electronic recipe is a customization of a previously stored electronic recipe, wherein the previously stored electronic recipe includes information indicating the first ingredient, a predetermined third mass of the first ingredient that is different from the first mass, the second ingredient, and a predetermined fourth mass of the second ingredient that is different from the second mass.

7. The system of claim 1, wherein the one or more processors are further configured by machine-readable instructions to facilitate selection, viewing, and following of the stored new electronic recipe via the user interface.

8. The system of claim 1, wherein the one or more processors are further configured by machine-readable instructions to determine nutritional information for the dish, the nutritional information comprising information related to one or more of calories, vitamins, or minerals in the masses of the individual ingredients added to the dish.

9. The system of claim 8, wherein the one or more processors are further configured by machine-readable instructions to facilitate presentation of the nutritional information for the dish via the user interface.

10. The system of claim 1, wherein the dish includes one or more of a plate, a bowl, a cup, or a tray.

11. A method for determining user-created recipes based on indications of individual ingredients added to a dish and determinations of masses of individual ingredients added to the dish during preparation, the method comprising:
  generating output signals conveying information related to the masses of the individual ingredients added to the dish, the individual ingredients including a first ingredient and a second ingredient, the second ingredient being added to the dish after the first ingredient, and
  obtaining ingredient information indicating which individual ingredient is currently being added to the dish, the ingredient information obtained from a user via a user interface, the ingredient information indicating whether the first ingredient or the second ingredient is being added to the dish;
  determining the masses of the individual ingredients added to the dish, the mass determinations based on the output signals,
    wherein, responsive to the obtained ingredient information indicating that the first ingredient is being added to the dish, a first mass of the first ingredient is determined, and
    responsive to the obtained ingredient information indicating that the second ingredient is being added to the dish, a second mass of the second ingredient is determined based on the first mass of the first ingredient and a total mass of the dish and
  electronically storing information that indicates both the individual ingredients and the determined masses of the individual ingredients in the dish in a new electronic recipe, such that information indicating the first ingredient, the first mass of the first ingredient, second ingredient, and the second mass of the second ingredient is stored in the new electronic recipe.

12. The method of claim 11, further comprising receiving, holding, and weighing the individual ingredients.

13. The method of claim 12, wherein the masses of the individual ingredients added to the dish are the weights of the individual ingredients added to the dish.

14. The method of claim 12, further comprising taring the scale before the first individual ingredient is added to the dish and before the second individual ingredient is added to the dish.

15. The method of claim 12, further comprising determining a weight of the second ingredient by subtracting a total weight of the first ingredient from a total weight of the dish.

16. The method of claim 11, wherein the new electronic recipe is a customization of a previously stored electronic recipe, wherein the previously stored electronic recipe includes information indicating the first ingredient, a predetermined third mass of the first ingredient that is different from the first mass, the second ingredient, and a predetermined fourth mass of the second ingredient that is different from the second mass.

17. The method of claim 11, further comprising facilitating selection, viewing, and following of the stored new electronic recipe via the user interface.

18. The method of claim 11, further comprising determining nutritional information for the dish, the nutritional information comprising information related to one or more of calories, vitamins, or minerals in the masses of the individual ingredients added to the dish.

19. The method of claim 18, further comprising facilitating presentation of the nutritional information for the dish via the user interface.

20. The method of claim 11, wherein the dish includes one or more of a plate, a bowl, a cup, or a tray.

21. A prompted recipe preparation system configured to determine user-created recipes based on prompts given to a user to cease adding individual ingredients to a dish during preparation, the system comprising:
  a scale configured to generate output signals conveying information related to masses of the individual ingredients added to the dish, the individual ingredients including a first ingredient and a second ingredient, the second ingredient being added to the dish after the first ingredient;
  a user interface configured to receive entry and/or selection of an electronic recipe for preparation by the user, the electronic recipe specifying target masses of the individual ingredients in the dish, such that the electronic recipe specifies a first target mass for the first ingredient and a second target mass for the second ingredient,
    wherein the user interface is configured to receive entry and/or selection of ingredient information indicating which individual ingredient is currently being added to the dish during preparation, the ingredient information indicating whether the first ingredient or the second ingredient is being added to the dish; and
  one or more processors configured by machine-readable instructions to:
    determine the masses of the individual ingredients added to the dish, the mass determinations based on the output signals from the scale;
    responsive to the masses of the individual ingredients added to the dish reaching the target masses of the individual ingredients specified by the electronic recipe, control the user interface to prompt the user to cease adding the individual ingredients, such that
      responsive to the mass of the first ingredient reaching the first target mass of the first ingredient, control the user interface to prompt the user to cease adding the first ingredient, and
      responsive to the mass of the second ingredient reaching the second target mass of the second ingredient, control the user interface to prompt the user to cease adding the second ingredient, the mass of the second ingredient determined based on the mass of the first ingredient and a total mass of the dish; and
    responsive to the masses of the individual ingredients added to the dish not matching the target masses of the individual ingredients specified by the electronic recipe, facilitate electronic storage of information that indicates both the individual ingredients and the determined masses of the individual ingredients in the dish in a new electronic recipe, such that
      responsive to the determined mass of the first ingredient being a first mass that is not the first target mass, and the determined mass of the second ingredient being a second mass that is not the second target mass, facilitate electronic storage of information indicating the first ingredient, the first mass of the first ingredient, the second ingredient, and the second mass of the second ingredient in the new electronic recipe.

22. The system of claim 21, wherein the scale is configured to receive, hold, and weigh the individual ingredients.

23. The system of claim 22, wherein the masses of the individual ingredients added to the dish are the weights of the individual ingredients added to the dish.

24. The system of claim 23, wherein the weights of the individual ingredients are current running totals of the weights of the individual ingredients added to the dish during preparation.

25. A method for determining user-created recipes based on prompts given to a user to cease adding individual ingredients to a dish during preparation, the method comprising:

generating output signals conveying information related to masses of the individual ingredients added to the dish, the individual ingredients including a first ingredient and a second ingredient, the second ingredient being added to the dish after the first ingredient;

receiving entry and/or selection of an electronic recipe for preparation by the user, the electronic recipe specifying target masses of the individual ingredients in the dish such that the electronic recipe specifies a first target mass for the first ingredient and a second target mass for the second ingredient, and receiving entry and/or selection of ingredient information indicating which individual ingredient is currently being added to the dish during preparation, the ingredient information indicating whether the first ingredient or the second ingredient is being added to the dish;

determining the masses of the individual ingredients added to the dish, the mass determinations based on the output signals, responsive to the masses of the individual ingredients added to the dish reaching the target masses of the individual ingredients specified by the recipe, prompting the user to cease adding the individual ingredients, such that responsive to the mass of the first ingredient reaching the first target mass of the first ingredient, the user is prompted to cease adding the first ingredient, and responsive to the mass of the second ingredient reaching the second target mass of the second ingredient, the user is prompted to cease adding the second ingredient, the mass of the second ingredient determined based on the mass of the first ingredient and a total mass of the dish; and responsive to the masses of the individual ingredients added to the dish not matching the target masses of the individual ingredients specified by the recipe, facilitating electronic storage of information that indicates both the individual ingredients and the determined masses of the individual ingredients in the dish in a new electronic recipe, such that responsive to the determined mass of the first ingredient being a first mass that is not the first target mass, and the determined mass of the second ingredient being a second mass that is not the second target mass, information indicating the first ingredient, the first mass of the first ingredient, the second ingredient, and the second mass of the second ingredient is stored in the new electronic recipe.

26. The method of claim 25, further comprising receiving, holding, and weighing the individual ingredients.

27. The method of claim 26, wherein the masses of the individual ingredients added to the dish are the weights of the individual ingredients added to the dish.

28. The method of claim 27, wherein the weights of the individual ingredients are current running totals of the weights of the individual ingredients added to the dish during preparation.

29. The system of claim 1, wherein the user provides the ingredient information without reference to a pre-existing recipe.

30. The system of claim 29, wherein the new electronic recipe is an experimental recipe determined by the user during preparation.

31. The method of claim 11, wherein the user provides the ingredient information without reference to a pre-existing recipe.

32. The method of claim 31, wherein the new electronic recipe is an experimental recipe determined by the user during preparation.

* * * * *